(12) United States Patent
Finarov et al.

(10) Patent No.: US 6,720,568 B2
(45) Date of Patent: Apr. 13, 2004

(54) METHOD AND SYSTEM FOR OPTICAL INSPECTION OF A STRUCTURE FORMED WITH A SURFACE RELIEF

(75) Inventors: Moshe Finarov, Rehovot (IL); Yoel Cohen, Ness Ziona (IL)

(73) Assignee: Nova Measuring Instruments Ltd., Rehovot (IL)

( * ) Notice: Subject to any disclaimer, the term of this patent is extended or adjusted under 35 U.S.C. 154(b) by 68 days.

(21) Appl. No.: 09/942,968

(22) Filed: Aug. 31, 2001

(65) Prior Publication Data

US 2002/0033450 A1 Mar. 21, 2002

(30) Foreign Application Priority Data

Aug. 31, 2000 (IL) .................................................. 138193

(51) Int. Cl.[7] .............................................. G01N 21/88
(52) U.S. Cl. ................................ 250/559.45; 356/237.1
(58) Field of Search .......................... 356/237.1, 237.2, 356/237.3, 237.4, 237.5, 630, 635, 450–451, 239.3, 239.7; 250/559.27, 559.4, 206, 559.22, 559.44–559.45, 559.3

(56) References Cited

U.S. PATENT DOCUMENTS 5,763,123 A * 6/1998 Shishido et al. ............... 430/30
5,872,633 A    2/1999 Holzapfel et al.
6,100,985 A * 8/2000 Scheiner et al. ............ 356/630
6,281,974 B1 * 8/2001 Scheiner et al. ............ 356/491
6,317,514 B1 * 11/2001 Reinhorn et al. ........... 382/147
6,476,920 B1 * 11/2002 Scheiner et al. ............ 356/630
6,603,529 B1 * 8/2003 Finarov ....................... 355/27

FOREIGN PATENT DOCUMENTS

WO   WO 00/12958   3/2000

* cited by examiner

Primary Examiner—David Porta
Assistant Examiner—Patrick J. Lee
(74) Attorney, Agent, or Firm—Browdy and Neimark

(57) ABSTRACT

A method and system are presented for inspecting a structure containing a pattern in the form of a surface relief fabricated by a pattern-creating tool applied to the structure. Reference data is provided being indicative of photometric intensities of light components of different wavelengths returned from a structure having a pattern similar to the pattern of the structure under inspection. Spectrophotometric measurements are continuously applied to successive locations within the surface relief on the structure so as to form a measurement slice thereon. Measured data in the form of a spectrum indicative of photometric intensities of light components of different wavelengths returned from the successive locations within the slice is detected and analyzed to determine whether it correlates with the reference data in accordance with predetermined criteria results.

24 Claims, 2 Drawing Sheets

METHOD AND SYSTEM FOR OPTICAL INSPECTION OF A STRUCTURE FORMED WITH A SURFACE RELIEF

FIELD OF THE INVENTION

This invention is generally in the field of optical measurement techniques, and relates to a method and system for optical inspection of a structure formed with a surface relief.

BACKGROUND OF THE INVENTION

The manufacture of semiconductor devices consists of several procedures applied to a semiconductor wafer to define active and passive elements. The wafer is prepared and one or more layers are deposited thereon. Thereafter, the process of photolithography is performed, in which the surface of a wafer is formed with a pattern conforming to circuit elements. An etching process applied to the uppermost layer follows the photolithography. By desirably repeating these processes, a multi-level semiconductor wafer is produced. Thus, photolithography is one of the main steps in the manufacture of semiconductor devices. It actually consists of the optical image transfer of a pattern from a mask to a semiconductor wafer. The major steps of the photolithography process are as follows:

- coating a wafer with a photoresist (PR) material followed by a backing procedure;
- exposing the PR to UV radiation through a mask in order to produce a latent image of the mask on the PR;
- developing the exposed PR in order to produce a pattern in the form of a plurality of spaced-apart PR-containing regions;
- etching consisting of removing the wafer layer underneath the PR layer within the spaces between the PR-containing regions;
- removing the PR layer; and
- measuring and inspecting the so-obtained patterned structure.

Thus, the structure undergoing the inspection is that resulting from the final etching procedure, i.e., with the complete layer pattern.

Techniques for monitoring the PR coating procedure have been developed, and is disclosed for example in WO 00/12958. According to this technique, which is based on spectrophotometric measurements, the latter are carried out in-situ during the coating and/or backing procedure. The measurements are applied to separate locations on the uppermost, unpatterned, PR-containing layer during the wafer spinning, and a conventional sampling is performed to determine the layer average result.

U.S. Pat. No. 5,872,633 discloses a technique for in-situ measurements carried out during a Chemical Mechanical Plananization (CMP) process, which provides actual thickness of the surface layer of a workpiece. According to this technique, measurements are performed during the rotation of the wafer under polishing. Because of repeating nature of die structure, the wafer surface may be advantageously samples for one full rotation of the wafer, and the measurements taken during that rotation suitable averaged to largely suppress or even cancel out the effect of the non-uniform topology of the dies beneath the uppermost layer (typically $SiO_2$) being polished. In other words, the existing pattern in the underlying layer(s) impedes the thickness measurements on the uppermost layer, and output signals associated with this pattern should therefore be suppressed.

SUMMARY OF THE INVENTION

There is a need in the art to facilitate inspection of the results of a PR development process, by providing a novel optical inspection method and system. This is associated with the fact that timely detection of defects introduced during the development stage enables to make corrections (reprocessing), if possible, to timely remove defected wafers from the production line, and/or provide feed-forward closed loop control of the coating/development tool.

Generally speaking, there is a need for a technique capable of measuring in patterned structures similar to those resulting from the PR development process. Moreover, this technique should be performed automatically, i.e., during the wafer movement through a phototrack (i.e., photolithography tools arrangement). A measurement system has to meet the footprint requirements of the conventional phototrack, and preferably eliminating the need for additional wafer handling means, in addition to those existing in the phototrack (i.e., robot or the like typically transporting the wafer between the photolithography tools).

Thus, the main idea of the present invention consists of continuously applying spectrophotometric measurements to a patterned structure progressing on a production line from a pattern-creating tool to a further station, and analyzing measured data to determine whether it satisfies certain criteria results or not.

The term "patterned structure" used herein signifies a structure formed with a surface relief in the form of a pattern containing a plurality of spaced-apart projecting regions defining pits within the spaces between these regions. Such a patterned structure may be composed of layers, in which case the pattern is in the form of spaced-apart regions of an uppermost layer spaced by regions of the underneath layer. The uppermost and underneath layers may have different optical properties, such as in semiconductor wafers.

The term "pattern-creating tool" signifies a processing tool applied to a structure to produce a surface relief thereon. Such a pattern-creating tool may be a developer tool or the combination of coater and developer tools typically used in the photolithography tools arrangement, etching tool, stamper used in the manufacture of CD or DVD, etc.

The term "criteria results" defines the final results of the technique to be obtained, and as used herein signifies certain predetermined characteristics of the pattern to be produced by the pattern-creating tool. These characteristics may be indicative of the absence (entire or partly) of the uppermost layer (e.g., photoresist), the thickness or non-uniformity of thickness of the patterned layer (e.g., the so-called "double coating" of the entire uppermost layer or its separate locations). Generally speaking, the characteristics of the pattern produced by the pattern-creating tool can be indicative of the quality of the pattern-creating process, and can therefore be used for process control, e.g., closed loop control (CLC).

There is thus provided according to one broad aspect of the present invention, a method for inspecting a structure containing a pattern in the form of a surface relief fabricated by a pattern-creating tool applied to structure, the method comprising:

(a) providing reference data indicative of photometric intensities of light components of different wavelengths returned from a structure having a pattern similar to said pattern of the structure under inspection;

(b) continuously applying spectrophotometric measurements to successive locations within the surface relief on the structure so as to inspect a slice thereon;

(c) detecting measured data in the form of a spectrum indicative of photometric intensities of light components of different wavelengths returned from the successive locations within the slice; and (d) analyzing the measured data to determine whether it correlates with said reference data in accordance with predetermined criteria results.

Preferably, the analysis of the measured data includes analysis of the shape of the detected spectrum, e.g., the number of picks.

The reference data may be obtained by prior inspection of the so-called "golden structure". Alternatively, an optical model could be utilized based on the known features of the pattern to be created by the tool. Such an optical model can be created on the basis of the known Rigoreous Coupled Wave Theory (RCWT).

Preferably, the continuous application of the spectrophotometric measurements is carried out during the movement of the structure from the pattern-creating tool towards the further station, with a spectrophotometer stationary mounted with respect to a conveying assembly supporting the structure during this movement.

The method can also comprise the step of analyzing the measured data with respect to working parameters of the pattern-creating tool, so as to enable a closed loop feedforward control of these parameters prior to applying the tool to a further similar structure.

Preferably, the pattern-creating tool is a photoresist developer used in the photolithography process applied to the structure, such as a semiconductor wafer.

Thus, according to another broad aspect of the present invention, there is provided a method for in-process inspecting of a semiconductor wafer comprising a surface relief of a developed photoresist layer, the method comprising the steps of (i) providing reference data indicative of photometric intensities of light components of different wavelengths returned from the wafer;

(ii) continuously applying spectrophotometric measurements to successive locations within the surface relief on the wafer so as to inspect a slice thereon;

(iii) detecting measured data in the form of a spectrum indicative of photometric intensities of light components of different wavelengths returned from the successive locations within the slice; and (iv) analyzing the measured data to determine whether it correlates with said reference data in accordance with predetermined criteria results.

There are also provided a method for controlling a process consisting of creating a pattern in the form of a surface relief on a structure, and a method for carrying out a photolithography process applied to a semiconductor wafer.

According to yet another aspect of the present invention, there is provided a system comprising a pattern-creating tool to be applied to a structure to form it with a surface relief, and a measurement unit operable for applying optical measurements to the patterned structure and carrying quality control of the surface relief.

According to yet another aspect of the invention, there is provided a photolithography tools arrangement for applying to a semiconductor wafer provided with an optical measurement unit and a translation unit operable to carry out a relative displacement of the wafer relative to an optical arrangement of the measurement unit during spectrophotometric measurements within a slice on the wafer.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

More specifically, the present invention is used for controlling a photolithography process used in the manufacture of semiconductor devices, and is therefore exemplified below with respect to this specific application.

Figure 1:
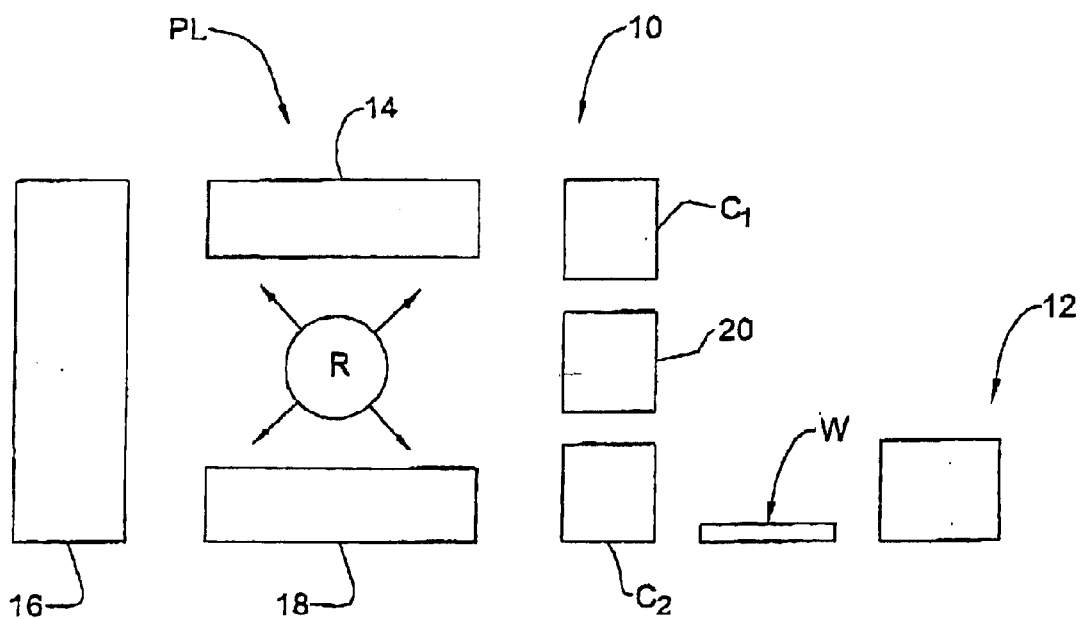
FIG. 1 schematically illustrates a part of a production line including a photolithography tool arrangement that utilizing a measurement system for carrying out a method of the invention, and an etching tool.

Referring to FIG. 1, there is illustrated a part of a production line PL showing a semiconductor wafer W progressing on the production line between a photolithography tools arrangement, generally designated 10 (i.e., a phototrack), and an etching tool 12 accommodated downstream of the phototrack. The phototrack is typically composed of such tools as a coater 14, an exposure tool 16, and a developer 18. A robot R (or number of robots) conveys wafers to be sequentially processed by these tools from a load cassette $C_1$ and returns processed wafers to an unload cassette $C_2$.

The construction and operation of these tools do not form part of the present invention, and therefore need not be specifically described, except to note the following. A photoresist (PR) layer is deposited onto a metal layer (or insulating substrate) within the coater 14, then PR layer is exposed to light and developed to create a pattern (surface relief) on the surface of the substrate. In other words, in this specific example, the exposure and developer tools present together a pattern-creating tool. It should be understood that either one of the tools in the arrangement 10, as well as the entire arrangement, whose working parameters affect the quality of the pattern, could constitute the pattern-creating tool.

As shown, a measurement system 20 is installed between the phototrack 10 and the etching tool 12, so as to be applied to wafers prior to entering the etching tool. The system 20 can be entirely integrated with the phototrack, or partly integrated, such that its optical arrangement to be applied to the wafer is located within the phototrack, while other elements (such as a light source, detector, and processor) are accommodated outside the phototrack in the proximity thereof. In the present example, the same robot R conveys wafers to and away from the measurement system. Moreover, the same robot may progressively support the wafer during measurements with the system 20.

Figure 2:
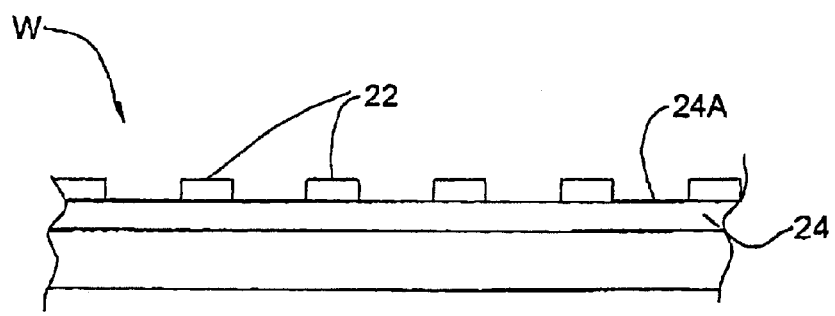
FIG. 2 is a schematic illustration of a patterned structure produced by a pattern-creating tool.

Turning now to FIG. 2, there is illustrated a wafer W as ensuing from the developer tool 14. The wafer W is a patterned structure, wherein the pattern is in the form of spaced-apart PR regions 22 on the surface 24a of a metal layer 24. It should be understood that, generally, a pattern is in the form of a surface relief of a layer, which may for example be produced by applying a stamper to the layer. Thus, in this specific example, the pattern-creating tool creates PR projections 22, aimed at etching metal regions within the spaces between these projections, and then removing the PR therefrom.

Figure 3:
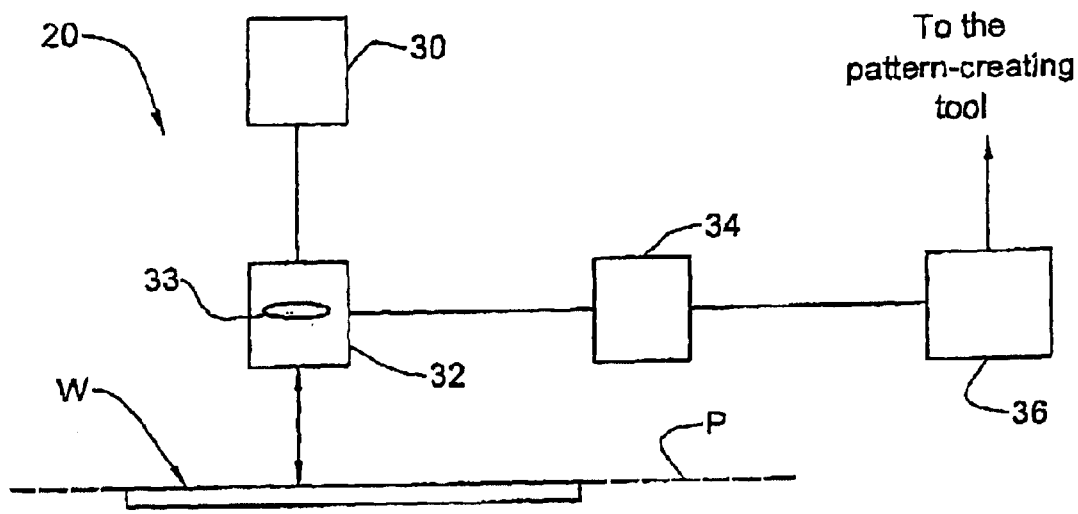
FIG. 3 is a block diagram of the main components of the measurement system of FIG. 2.

Reference is made to FIG. 3, illustrating the measurement system 20. The latter is composed of such main constructional parts as an illumination unit 30 of a kind capable of illuminating the wafer with different wavelengths (i.e., the broad band illumination); a light direction/collecting optics 32 typically including an objective lens 33 or a plurality of such lenses; a detection unit 34 including a spectrophotometer; and a control unit 36.

The construction and operation of the illumination and detection units, as well as the light direction/collecting optics, are also known per se and therefore need not be specifically described.

The control unit is typically a computer system having a memory for storing reference data, a processor operating by suitable software for analyzing measured data generated by the spectrophotometer, and a monitor for displaying measurement results. The analysis of the measured data may include comparison thereof to the reference data, and/or to theoretical data produced by an optical model.

As shown in FIG. 3, the control unit 36 is connectable to the pattern-creating tool (or its relevant part, e.g., developer), thereby enabling to utilize the analysis results for carrying out a closed loop control of the pattern-creating tool. The analysis of the measured data (spectrum) is indicative of the quality of the pattern, and consequently, indicative of the quality of the pattern-creation process defined by the working parameters of the pattern-creating tool. Hence, the measurement results may be used for the so-called "feed forward" closed loop control of these working parameters prior to applying the tool to a further similar wafer (i.e., the same-lot-wafer).

The measurement system operates in the following manner. During the translation of the wafer from the developer tool to the unload cassette, optical measurements are applied to one or more slices on the wafer's surface. The wafer is supported either by robot R, or by an additional translation stage, for providing reciprocating or rotation of the wafer with respect to the objective lens arrangement within a measurement plane P. It should be understood, that alternatively, the wafer may be kept stationary in the plane P, and a relevant part of the optical system be displaced with respect to the wafer.

During the relative displacement of the wafer relative to the objective lens arrangement, measurements are carried out continuously so as to detect light returned from successive locations on the wafer within a slice. Resulting measured data is in the form of a spectrum, i.e., a photometric intensity of the returned light as a function of wavelengths. This spectrum is analyzed by correlating it with the reference data, the certain extent of correlation presenting the criteria results. The minimal spot size should be larger than the dimensions of the largest element of the pattern (feature in the die).

The measurement slice may extend across the wafer, along its radius, be spiral-like, etc. The measurement slice is a segment on the wafer for which measured data is obtained. One or more slices may be measured for the inspection purposes. The length of the slice is determined by the spot size (defined by the measurement unit) and by the type of pattern in the structure. In the specific example of wafer inspection, the minimal length $L_{min}$ of the slice should satisfy the following condition: $L_{min} > S_{die}/d$, wherein $S_{die}$ is the surface area occupied by one die, and d is the diameter of the light spot. Maximal time t needed for passing one slice is determined by the saturation time $t_{sat}$ of the spectrophotometer (specific sensor's parameter) within the selected range of operating wavelengths, namely, should satisfy the following condition: $t < t_{int}$. As for the sufficient signal-to-noise ratio of the detected signals, it is determined by an integration time $t_{int}$ (defined by the system or operator).

It should be noted that measurements should preferably be carried out during the uniform motion of the wafer or optics (i.e., without acceleration). To this end, if accelerated motion paths of the wafer under measurements exist (typically when entering and ensuing from the measurement zone), they should be disregarded when analyzing the measured data.

Figure 4:
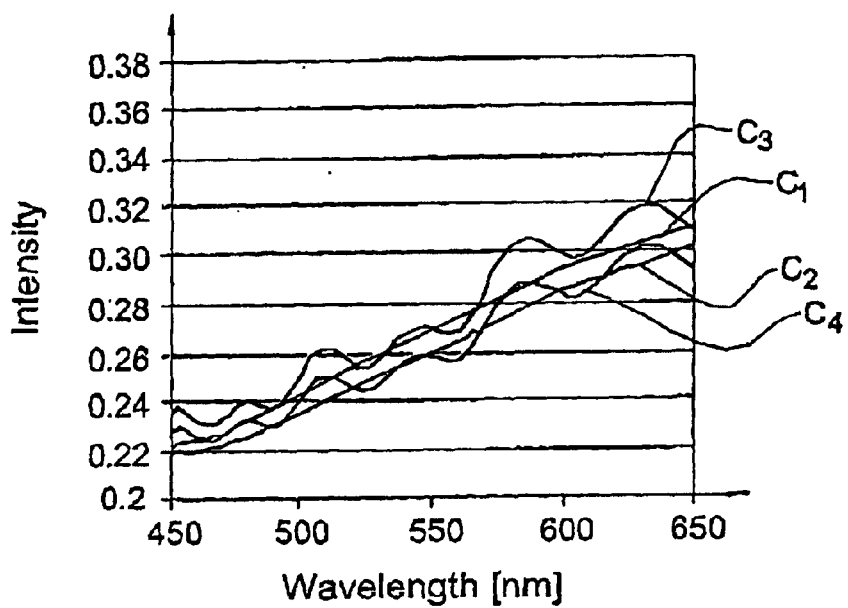
FIG. 4 graphically illustrates the measurement results.

FIG. 4 presents the measured data obtained with the above system utilizing the MMS1/VIS-ENL spectrophotometer commercially available from Carl Zeiss. The measured data is in the form of four curves $C_1$–$C_4$, each presenting a photometric intensity of the detected light as a function of wavelength. Curves $C_1$ and $C_2$ correspond to uncoated metal layer (i.e., without PR pattern) obtained for two different, same-lot wafers $W_1$ and $W_2$, respectively. Curves $C_3$ and $C_4$ correspond to PR-patterned wafers (i.e., after development) $W_3$ and $W_4$, respectively. It should be understood that the pair of wafers $W_3$ and $W_4$ could be the same wafers $W_1$ and $W_2$, but at different manufacturing stages with different parameters (e.g., PR thickness), presenting thereby different patterned structures. Curves $C_1$ and $C_2$ are characterized by 0.9953 correlation; curves $C_3$ and $C_4$ are characterized by 0.9940 correlation; and curves $C_1$ (or $C_2$) and $C_3$ are characterized by 0.9749 correlation. This actually demonstrates that the technique of the present invention provides meaningful results. As clearly seen in the figure, the detected spectra $C_3$ and $C_4$ have very similar shapes, i.e., the same number of picks and pitch.

Hence, by providing reference data in the form of spectrum (obtained either with a golden wafer at various manufacturing steps or with an optical model), the measured data obtained with a wafer under inspection can be fitted to the "theoretical" data (reference data). This enables to estimate the quality of the patterned layer (e.g., developed PR).

Those skilled in the art will readily appreciate that various modifications and changes can be applied to the preferred embodiment of the invention as hereinbefore exemplified without departing from its scope defined in and by the appended claims.

What is claimed is:

1. A method for inspecting a structure containing a pattern in the form of a surface relief fabricated by a pattern-creating tool applied to the structure, the method comprising:

(a) providing reference data indicative of a spectrum of photometric intensities of broad band light components of different wavelengths returned from a structure having a pattern similar to said pattern of the structure under inspection;

(b) continuously applying spectrophotometric measurements with broad band illumination to successive locations within the surface relief on the structure along a measurement slice thereon;

(c) detecting measured data in the form of a single spectrum indicative of photometric intensities of light components of different wavelengths returned from the successive locations within the slice; and (d) analyzing the measured data to determine whether it correlates with said reference data in accordance with predetermined criteria results.

2. The method according to claim 1, wherein the analyzing of the measured data comprises analyzing a shape of the detected spectrum.

3. The method according to claim 2, wherein the shape of the detected spectrum is defined by a number of peaks in the detected spectrum.

4. The method according to claim 1, wherein the reference data is provided by applying steps (b) and (c) to a structure substantially identical to the structure under inspection.

5. The method according to claim 1, wherein the reference data is provided by applying an optical model based on some known features of the structure under inspection.

6. The method according to claim 1, wherein the continuous spectrophotometric measurements are carried out, while relatively displacing the structure with respect to an optical arrangement of a spectrophotometer.

7. The method according to claim 6, wherein the analyzed measured data is that obtained during substantially uniform relative displacement of the structure.

8. The method according to claim 1, wherein said slice is a substantially straight line.

9. The method according to claim 1, wherein said slice is a curve.

10. The method according to claim 1, wherein a minimal length of said slice is determined by a spot size of incident light, and by a type of the pattern.

11. The method according to claim 1, wherein a maximal time t for continuously measuring within the measurement slice is determined by a saturation time $t_{sat}$ of a spectrophotometer within the selected range of operating wavelengths, such as to satisfy a condition: $t<t_{sat}$.

12. The method according to claim 1, and also comprising the step of analyzing the measured data with respect to working parameters of the pattern-creating tool, thereby enabling a closed loop control of said parameters.

13. The method according to claim 12, wherein said closed loop control is carried out in a feed-forward manner prior to applying the tool to a further similar structure.

14. The method according to claim 1, wherein the pattern-creating tool is included in a photolithography tools arrangement.

15. The method according to claim 14, wherein said structure is a semiconductor wafer.

16. The method according to claim 15, wherein a minimal length $L_{min}$ of the slice satisfies a condition: $L_{min}>S_{die}/d$, wherein $S_{die}$ is a surface area occupied by one die, and d is a diameter of a light spot of incident light.

17. The method according to claim 14, wherein said pattern-creating tool is a photoresist developer.

18. A method for in-process inspecting of a semiconductor wafer comprising a surface relief of a developed photoresist layer, the method comprising:

(i) providing reference data indicative of a spectrum of photometric intensities of broad band light components of different wavelengths returned from the wafer;

(ii) continuously applying spectrophotometric measurements with broad band illumination to successive locations within the surface relief on the wafer along a measurement slice thereon;

(iii) detecting measured data in the form of a single spectrum indicative of photometric intensities of light components of different wavelengths returned from the successive locations within the slice; and (iv) analyzing the measured data to determine whether it correlates with said reference data in accordance with predetermined criteria results.

19. The method according to claim 18, wherein said surface relief of the developed photoresist is formed on a metal layer beneath the photoresist layer.

20. A method for carrying out a photolithography process applied to a semiconductor wafer, the method comprising:

coating the wafer with a photoresist layer;

exposing the photoresist layer;

developing the exposed layer, thereby creating a pattern in the form of a surface relief; and continuously applying spectrophotometric measurements with broad band illumination to successive locations within a surface relief of the wafer, detecting measured data in the form of a single spectrum indicative of photometric intensities of light components of different wavelengths returned from the successive locations along a slice, and analyzing the measured data so as to determine whether it correlates with reference data in accordance with predetermined criteria results.

21. A method for controlling a process consisting of creating a pattern in the form of a surface relief on a structure, the method comprising:

providing reference data indicative of photometric intensities of broad band light components of different wavelengths returned from a structure having a pattern similar to the pattern to be created;

continuously applying spectrophotometric measurements with broad band illumination to successive locations within the surface relief on the structure along a measurement slice thereon;

detecting measured data in the form of a single spectrum indicative of photometric intensities of light components of different wavelengths returned from the successive locations within the slice;

analyzing the measured data to determine whether it correlates with said reference data in accordance with predetermined criteria results; and utilizing analysis results for closed loop control of the pattern creation process.

22. A system comprising a pattern-creating tool to be applied to a structure to create a pattern thereon in the form of a surface relief, and a measurement unit operable for applying optical measurements to the patterned structure and carrying quality control of the surface relief, the system comprising:

a translation unit operable to carry out a relative displacement between the patterned structure and an optical arrangement of the measurement unit;

a spectrophotometer operable to apply spectrophotometric measurements by illuminating the structure with broad band light, detecting light returned from the illuminated structure, and generating a measured spectral data indicative thereof; and a control unit that operates said translation unit to provide said relative displacement to sequentially bring to the measurements successive locations along a slice on the structure, and operates said spectrophotometer to continuously apply the spectrophotometric measurements during said displacement, said measured data being thereby indicative of a single spectrum of photometric intensities of light components of different wavelengths returned from the successive locations along the slice, the control unit operating to be responsive to the measured data and analyzes it with respect to reference data indicative of photometric intensities of light components of different wavelengths returned from a structure having a pattern similar to said pattern of the structure under inspection, so as to determine a correlation between the measured data and reference data in accordance with predetermined criteria results.

23. The system according to claim 22, wherein said control unit is connectable to the pattern-creating tool, thereby enabling to utilize analysis results for closed loop control of working parameters of the pattern-creating tool.

24. A photolithography tools arrangement to be applied to a semiconductor wafer to create a pattern thereon in the form of a surface relief of a developed photoresist, the arrangement being provided with an optical measurement unit and a translation unit operable to carry out a relative displacement between the wafer and an optical arrangement of the measurement unit, the measurement unit comprising:

- a spectrophotometer operable to apply spectrophotometric measurements to the structure by illuminating the structure with broad band light, detect light returned from the illuminated structure, and generate a measured data indicative thereof; and
- a control unit that operates said translation unit to provide said relative displacement so as to sequentially bring to the measurements successive locations along a slice on the structure, and operates said spectrophotometer to continuously apply the spectrophotometric measurements during said displacement, said measured data being thereby indicative of a single spectrum of photometric intensities of light components of different wavelengths returned from the successive locations along the slice, the control unit operating to be responsive to the measured data and analyzes it with respect to reference data indicative of photometric intensities of light components of different wavelengths returned from a structure having a pattern similar to said pattern of the structure under inspection, and determine a correlation between the measured data and reference data in accordance with predetermined criteria results.

* * * * *